United States Patent
Moon et al.

(10) Patent No.: US 10,241,469 B2
(45) Date of Patent: Mar. 26, 2019

(54) MORPHOLOGICAL CELL PARAMETER-BASED RED BLOOD CELL TEST METHOD AND DIGITAL HOLOGRAPHIC MICROSCOPE USED THEREIN

(71) Applicant: Industry-Academic Cooperation Foundation, Chosun University, Gwangju (KR)

(72) Inventors: Inkyu Moon, Gwangju (KR); Keyvan Jaferzadeh, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 39 days.

(21) Appl. No.: 15/284,539

(22) Filed: Oct. 4, 2016

(65) Prior Publication Data
US 2017/0357211 A1 Dec. 14, 2017

(30) Foreign Application Priority Data
Jun. 14, 2016 (KR) .................. 10-2016-0073948

(51) Int. Cl.
*G06K 9/00* (2006.01)
*G03H 1/00* (2006.01)
(Continued)

(52) U.S. Cl.
CPC ....... *G03H 1/0005* (2013.01); *G01N 15/1475* (2013.01); *G03H 1/0404* (2013.01);
(Continued)

(58) Field of Classification Search
CPC .......... G06T 2207/30024; G06T 7/521; G06K 9/00147; G06K 9/0014; G06K 9/00134; G06K 9/00127; G01N 15/1475
See application file for complete search history.

(56) References Cited

U.S. PATENT DOCUMENTS

| 7,616,320 | B2* | 11/2009 | Javidi | G01B 9/021 356/457 |
| 2008/0201083 | A1* | 8/2008 | Hata | G06T 7/0012 702/21 |
| 2012/0194649 | A1* | 8/2012 | Javidi | G06K 9/6247 348/50 |

FOREIGN PATENT DOCUMENTS

KR   10-2005-0035542 A   4/2005

OTHER PUBLICATIONS

Memmolo et al ("3D Morphometry of Red Blood Cells by Digital Holography", 2014).*
Rappaz et al. ("Comparative Study of Human Erythrocytes by Digital Holographic Microscopy, Confocal Microscopy, and Impedance Volume Analyzer", 2008).*

(Continued)

*Primary Examiner* — Avinash Yentrapati
(74) *Attorney, Agent, or Firm* — Hauptman Ham, LLP (57) ABSTRACT

Provided are a morphological cell parameter-based erythrocyte test method and digital holographic microscope used therein, and the morphological cell parameter-based erythrocyte test method includes performing modeling to create a 3D image of an erythrocyte to be tested and measuring morphological parameters of the erythrocyte based on the 3D image.

The morphological cell parameter-based erythrocyte test method performs modeling of a 3D image for an erythrocyte to be tested and measures morphological parameters of the erythrocyte based on the 3D image. Therefore, time and effort consumed in measurement may be reduced, and accuracy of the measurement is excellent.

11 Claims, 7 Drawing Sheets
(5 of 7 Drawing Sheet(s) Filed in Color)

(51) Int. Cl.
| | |
|---|---|
| *G03H 1/04* | (2006.01) |
| *G01N 15/14* | (2006.01) |
| *G06T 7/00* | (2017.01) |
| *G06T 7/60* | (2017.01) |
| *G06T 15/08* | (2011.01) |
| *G03H 1/08* | (2006.01) |
| *G06K 9/52* | (2006.01) |
| *G01N 15/00* | (2006.01) |
| *G01N 15/10* | (2006.01) |

(52) U.S. Cl.
CPC ......... *G03H 1/0443* (2013.01); *G03H 1/0866* (2013.01); *G06K 9/0014* (2013.01); *G06K 9/00134* (2013.01); *G06K 9/52* (2013.01); *G06T 7/0012* (2013.01); *G06T 7/602* (2013.01); *G06T 15/08* (2013.01); *G01N 2015/0073* (2013.01); *G01N 2015/1006* (2013.01); *G01N 2015/1454* (2013.01); *G03H 2001/005* (2013.01); *G03H 2001/0452* (2013.01); *G03H 2001/0471* (2013.01); *G03H 2210/30* (2013.01); *G06T 2207/10056* (2013.01); *G06T 2207/20036* (2013.01); *G06T 2207/30101* (2013.01)

(56) References Cited

OTHER PUBLICATIONS

Moon, Inkyu, et al. "Automated statistical quantification of three-dimensional morphology and mean corpuscular hemoglobin of multiple red blood cells." Optics express 20.9 (2012): 10295-10309.*

Inkyu Moon, Faliu Yi, Yeon H. Lee, Bahram Javidi, Daniel Boss, and Pierre Marquet, "Automated quantitative analysis of 3D morphology and mean corpuscular hemoglobin in human red blood cells stored in different periods," Opt. Express 21, 30947-30957 (2013).*

Keyvan Jaferzadeh et al., "Quantitative investigation of red blood cell three-dimensional geometric and chemical changes in the storage lesion using digital holographic microscopy," Journal of Biomedical Optics, Nov. 2015, vol. 20(11), Republic of Korea, 11 pages.

Moon et al., "Automated quantitative analysis of 3D morphology and mean corpuscular hemoglobin in human red blood cells stored in different periods." Optics Express 30947; Dec. 16, 2013; 12 pages; vol. 21, No. 25.

Moon et al., "Automated statistical quantification of three-dimensional morphology and mean corpuscular hemoglobin of multiple red blood cells." Optics Express 10295; Apr. 23, 2012; 16 pages; vol. 20, No. 9.

Korean Office Action dated Nov. 25, 2017 in connection with the counterpart Korean Patent Application No. 10-2016-0073948.

* cited by examiner

MORPHOLOGICAL CELL PARAMETER-BASED RED BLOOD CELL TEST METHOD AND DIGITAL HOLOGRAPHIC MICROSCOPE USED THEREIN

CROSS-REFERENCE TO RELATED APPLICATION

This application claims priority to and the benefit of Korean Patent Application No. 10-2016-0073948, filed on Jun. 14, 2016, the disclosure of which is incorporated herein by reference in its entirety.

BACKGROUND

1. Field of the Invention

The present invention relates to a morphological cell parameter-based erythrocyte test method and a digital holographic microscope used therein, and more particularly, to a morphological cell parameter-based erythrocyte test method, which includes performing modeling to create a three-dimensional (3D) image of an erythrocyte to be tested and measuring morphological parameters of the erythrocyte based on the 3D image, and a digital holographic microscope used therein.

2. Discussion of Related Art

It is known that erythrocytes are composed of water and proteins and are rich in hemoglobins, lipids and carbohydrates. The cell membrane of an erythrocyte is composed of water, proteins, lipids and carbohydrates. In terms of morphology, mature erythrocytes are a main cell type in blood in circulation. An erythrocyte is formed in an oval biconcave shape (often called oval disc-shape erythrocytes) having a flexible membrane which is best for maximum deformability, maximum surface relative to a predetermined volume, and rapid change, when the electrolyte passes through small capillaries during microcirculation.

Particularly, the biconcave shape of the erythrocyte does not have a complicated inner structure, which is considered to minimize free energy of the membrane with the limited area and volume. Erythrocytes need to be adjustable to a relatively wide size range of capillaries found in blood vessels, but need to, at the same time, maintain cellular integrity and functionality and be deformable. This is because erythrocytes do not have a 3D cytoskeleton, whose shape and mechanical integrity are maintained due to a 2D triangle lattice formed by a flexible spectrin tetramer. The spectrin tetramer is linked by an actin oligomer. Since the side length (70 to 80 nm) of actin is shorter than the contour length (approximately 200 nm) of the spectrin tetramer, it is considered that the spectrin affects bending modulus or curvature, as an essential contributor.

While a biochemical method has conventionally been used to measure morphological parameters with respect to erythrocytes composed of the above-described components, it takes much time to measure the parameters because such a biochemical method is complicated in terms of measurement and calculation of parameter values.

PRIOR ART

Patent Document (Patent Document 1) Korean Unexamined Patent Application Publication No. 10-2005-0035542: Blood test method

SUMMARY OF THE INVENTION

The present invention is invented to improve the above-described problem and, therefore, is to directed to providing a morphological cell parameter-based erythrocyte test method, which includes performing modeling to create a 3D image of an erythrocyte to be tested and measuring morphological parameters of the erythrocyte based on the 3D image, and a digital holographic microscope used therein.

In one aspect, the present invention provides a morphological cell parameter-based erythrocyte test method, which includes performing modeling to create a 3D image of an erythrocyte to be tested and measuring morphological parameters of the erythrocyte based on the 3D image.

In the modeling step, a 3D image is obtained from the erythrocyte to be tested by digital holographic microscopy.

The modeling step includes a hologram creating step for creating a holographic image by generating an optical interference signal from an object beam penetrating the erythrocyte and a reference beam emitted from a light source unit and taking an image of the optical interference signal using an imaging unit, and a 3D image creating step for performing modeling to create a 3D image of the erythrocyte based on the holographic image created in the hologram creating step.

In the hologram creating step, the object beam may pass through the erythrocyte from bottom to top.

In the hologram creating step, the object beam is penetrated through an erythrocyte in a direction crosslinked with the radius of the erythrocyte to obtain a holographic image of the concave part in the middle of the disc-shaped erythrocyte with a predetermined radius.

In the parameter measuring step, as the morphological parameter, a ratio of a thickness value of the 3D image at the position corresponding to the center of the erythrocyte with respect to a thickness value of the 3D image at the position corresponding to half of the radius of the erythrocyte is calculated from the center to the radius of the erythrocyte.

In the parameter measuring step, a morphological functionality factor of the erythrocyte, which is a ratio of a surface area of the erythrocyte with respect to a surface area of a sphere with a radius corresponding to the radius of the erythrocyte, may be calculated as the morphological parameter.

The surface area of the erythrocyte is the sum of a projected surface area of the 3D image and a top-view surface area of the 3D image.

The projected surface area (PSA) of the 3D image is calculated by the mathematical formula as follows: $PSA=N_p{}^2$, where p is the length of one side of pixels forming the 3D image, and N is the number of pixels forming the 3D image.

The surface area ($S_S$) of the sphere with a radius corresponding to the radius of the erythrocyte is calculated by the mathematical formula as follows: $S_S=4\pi r^2$, where r may be the radius of the erythrocyte.

The radius (r) of the erythrocyte is calculated by the mathematical formula as follows:

$$r \cong \sqrt{\frac{PSA}{\pi}}$$

where PSA is a projected surface area of the 3D image, which is a value obtained by multiplying the square of one side length of a pixel forming the 3D image by the number of pixels forming the 3D image.

In the parameter measuring step, as the morphological parameter, a sphericity index (SP) may also be calculated from a volume (V) of the 3D image and the surface area (SA) of the electrolyte using the mathematical formula as follows:

$$SP = \frac{4\pi V^{2/3}}{4\pi/3^{2/3}SA}.$$

The surface area (SA) of the electrolyte may be the sum of the projected surface area of the 3D image and the top-view surface area of the 3D image.

In the parameter measuring step, as the morphological parameter, the projected surface area (PSA) of the erythrocyte was calculated from the length (p) of one side of pixels of the 3D image and the number (N) of pixels forming the 3D image using the mathematical formula as follows: $PSA = N_p^2$.

In the parameter measuring step, as the morphological parameter, the surface area of the erythrocyte, which is the sum of the projected surface area of the erythrocyte and the top-view surface area of the 3D image, was calculated.

The morphological cell parameter-based erythrocyte test method according to the present invention may further include a prediction step for predicting a state of the erythrocyte based on the morphological parameter measured in the parameter measuring step.

Also, in the modeling step, numerous erythrocyte samples are subjected to modeling of 3D images, respectively, in the parameter measuring step, morphological parameters of each erythrocyte sample are measured based on the 3D images of the erythrocyte samples, and in the prediction step, a storage period after collection of the erythrocyte sample may be predicted based on the morphological parameters of each erythrocyte sample.

Meanwhile, the digital holographic microscope according to the present invention includes a light source unit for generating an object beam and a reference beam and irradiating the object beam to penetrate an erythrocyte to be tested, a beam splitter for generating an optical interference signal by receiving the object beam passing through the electrolyte and the reference beam, and an imaging unit for taking an image of the optical interference signal generated from the beam splitter in order to generate the object beam and the reference beam. The light source unit may emit the object beam in a direction crosslinked with the radius of the erythrocyte to obtain an image of the concave part in the middle of the disc-shaped erythrocyte with a predetermined radius.

Also, the digital holographic microscope according to the present invention further includes a setting plate which is formed of a light-penetrating material to allow the object beam to pass through and on which the erythrocyte is set with the concave part upward, and in the light source unit, the object beam is irradiated to penetrates the setting plate from bottom to top.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, a morphological cell parameter-based erythrocyte test method and a digital holographic microscope used therein according to exemplary embodiments of the present invention will be described in detail with reference to the accompanying drawings. The present invention can be modified and implemented in various forms, and therefore, only specific embodiments will be described in detail. However, the present invention is not limited to specific disclosures, and it should be understood that the present invention includes all modifications, equivalents, and alternatives included in the technical idea and scope of the present invention. In describing each of the drawings, like reference numerals are used to denote like elements. In the accompanying drawings, the dimensions of the structures are enlarged from actual sizes for clarity of the present invention.

The terms "first" and "second" may be used to explain various components, but the components should not be limited by these terms. The terms are used only to distinguish one component from another component. For example, without departing from the scope of the present invention, a first component may be called a second component, and similarly, a second component may be called a first component.

The terms used in the present invention are used only to explain specific examples, not to limit the present invention. Singular expressions include plural referents unless clearly indicated otherwise in the context. The term "include" or "have" used herein designate the presence of characteristics and components described in the specification, and do not imply that one or more other characteristics or components are excluded.

All terms including technical and scientific terms have the same meaning that is generally understood by those skilled in the art unless defined otherwise. General terms, such as terms defined in dictionaries, should be interpreted with meanings according to the context of related technology and should not be interpreted with ideal or excessively formal meanings unless they are clearly defined thus in the present invention.

Figure 1:
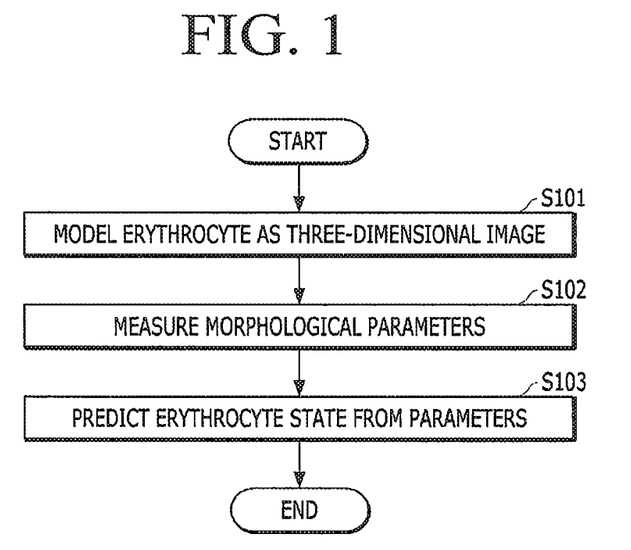
FIG. 1 is a flowchart illustrating a morphological cell parameter-based erythrocyte test method according to the present invention.

FIG. 1 shows a flowchart illustrating a morphological cell parameter-based erythrocyte test method according to the present invention.

Referring to FIG. 1, the morphological cell parameter-based erythrocyte test method includes a modeling step (S101), a parameter measuring step (S102), and a prediction step (S103).

The modeling step (S101) is for creating a 3D image of an erythrocyte to be tested. The modeling step (S101) is for obtaining a 3D model image from the erythrocyte to be tested by a digital holographic microscopy shown in FIG. 2 and includes a hologram creating step and a 3D image creating step.

Figure 2:
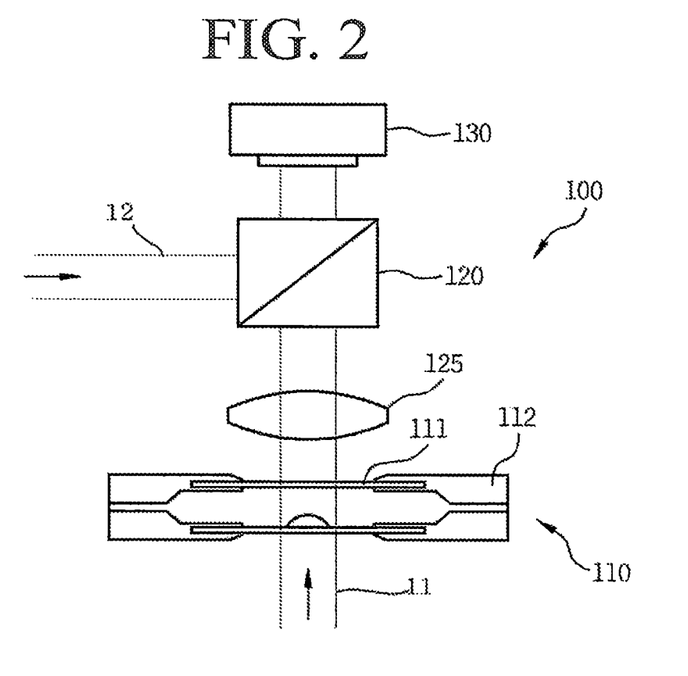
FIG. 2 is a concept diagram of a digital holographic microscope which is used in the morphological cell parameter-based erythrocyte test method according to the present invention.

The digital holographic microscope 100 will be described in further detail.

The digital holographic microscope 100 according to the present invention includes a setting plate 110 on which erythrocytes to be tested are set, a light source unit for generating an object beam 11 and a reference beam 12, and emitting the object beam 11 to penetrate the erythrocytes to be tested, a beam splitter 120 for generating an optical interference signal by receiving the object beam 11 passing through the erythrolytes and the reference beam 12, and an imaging unit 130 for taking an image of the optical interference signal generated from the beam splitter 120.

The setting plate 110 is formed of a material through which the object beam 11 passes and includes a plurality of penetration plates 111 supported to be spaced apart from each other in a vertical direction by a spacing member 112. A seating area in which blood including erythrocytes is seated is created between the penetration plates 111. The disc-shaped erythrocytes with a predetermined radius have the concave part in the middle and may be set to place the concave part upward between the penetration plates 111.

The light source unit is not illustrated in the drawing but includes a first light source which is equipped below the setting plate 110 to emit the object beam 11 to the setting plate 110, and a second light source for emitting the reference beam 12 onto an optical path of the object beam 11 that has penetrated the setting plate 110. The first and second light sources may generate laser beams with a wavelength of 682 nm as the object beam 11 and the reference beam 12, respectively.

Here, the light source unit may emit the object beam 11 to penetrate an erythrocyte in a direction crosslinked with the radius of the erythrocyte in order to obtain a holographic image of the concave part in the middle of the erythrocyte.

The beam splitter 120 is equipped at the position in which the optical path of the object beam 11 is crosslinked with the optical path of the reference beam 12 to generate an optical interference signal from the object beam 11 passing through the erythrocyte and the reference beam 12. The beam splitter 120 is one that is conventionally used in a digital holographic microscope 100 to generate the optical interference signal between the object beam 11 and the reference beam 12, and thus detailed descriptions thereof are omitted.

Here, an objective lens is equipped between the beam splitter 120 and the setting plate 110 over the optical path of the object beam 11. The objective lens may have a magnification of 40× and a field of view of 150 μm.

The imaging unit is equipped over the beam splitter 120 to take an image of the optical interference signal generated by the beam splitter 120, and a CCD camera is used in the imaging unit.

The hologram creating step is for generating the optical interference signal from the object beam 11 passing through the erythrocyte and the reference beam emitted from the light source unit and creating a holographic image by taking an image of the optical interference signal using the imaging unit 130. The light source unit is operated to generate the object beam 11 and the reference beam 12, and the optical interference signal generated through the beam splitter 120 is taken as a holographic image. Here, an examiner may set an erythrocyte on the setting plate 110 to place the concave part upward or may select only the erythrocyte set to place the concave part upward from erythrocyte objects included in the captured image as a test subject.

Figure 3:
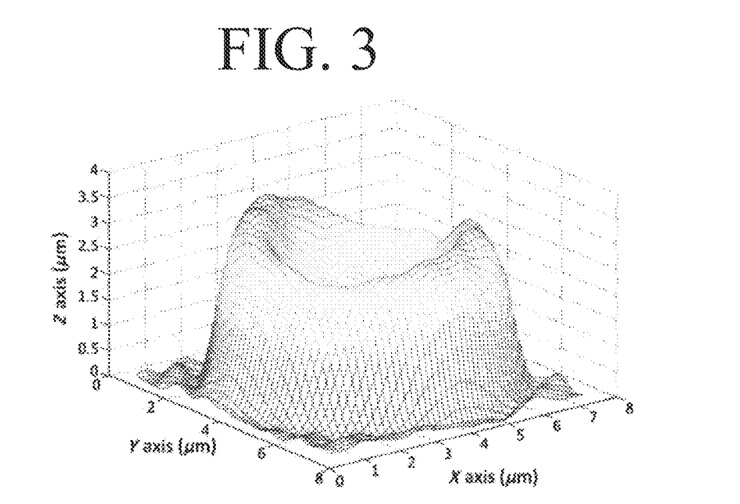
FIG. 3 is a 3D image of an erythrocyte, which is created by modeling by the morphological cell parameter-based erythrocyte test method according to the present invention.

The 3D image creating step is for performing modeling to create a 3D image of the erythrocyte based on the holographic image created in the hologram creating step. FIG. 3 shows a 3D image created by modeling the holographic image of the erythrocyte sample.

The parameter measuring step (S102) is for measuring morphological parameters of the erythrocyte from the 3D image. Here, the morphological parameters include the sphericity coefficient (k) of the erythrocyte, the projected surface area (PSA) of the erythrocyte, the surface area (SA) of the erythrocyte, the morphological functionality factor (f) of the erythrocyte, the volume of the erythrocyte, and the sphericity index of the erythrocyte.

The sphericity coefficient (k) of the erythrocyte is calculated by the mathematical formula 1 below.

$$k = \frac{d_c}{d_r} \quad \text{[Mathematical Formula 1]}$$

Here, $d_c$ is a thickness value of the 3D image at the position corresponding to the center of the erythrocyte, and dr is a thickness value of the 3D image at the position corresponding to the half of the radius of the erythrocyte from the center to the radius of the erythrocyte. That is, the sphericity coefficient (k) of the erythrocyte may be a ratio of a thickness value of the 3D image at the position corresponding to the center of the erythrocyte with respect to a thickness value of the 3D image at the position corresponding to half of the radius of the erythrocyte from the center to the radius of the erythrocyte.

The sphericity coefficient of the erythrocyte represents the shape of the erythrocyte center. It may be determined that, when the sphericity coefficient is less than 1, a concave part is created in the middle of the erythrocyte, when the sphericity coefficient is 1, the center of the erythrocyte is flat, and when the sphericity coefficient is higher than 1, the center of the erythrocyte is convex.

The projected surface area (PSA) of the erythrocyte is calculated by the mathematical formula 2 below.

$$PSA = Np^2 \quad \text{[Mathematical Formula 2]}$$

Here, p is a length of one side of pixels forming the 3D image, and N is the number of pixels in the range corresponding to the erythrocyte of the 3D image. In the 3D image of FIG. 2, p is 0.159 μm, and PSA is 45±5 μm². The projected surface area (PSA) of the erythrocyte is overall reduced as the storage period increases since blood collection.

Here, the radius (r) of the erythrocyte may be calculated from the projected surface area (PSA) of the erythrocyte by the mathematical formula 3.

$$r \cong \sqrt{\frac{PSA}{\pi}} \qquad \text{[Mathematical Formula 3]}$$

Also, the surface area (SA) of the erythrocyte may be obtained from the projected surface area (PSA) of the erythrocyte and is calculated by the mathematical formula 4.

$$SA = PSA + TVSA \qquad \text{[Mathematical Formula 4]}$$

Here, TVSA is a top-view surface area of the part corresponding to the erythrocyte of the 3D image and may be calculated through the 3D image shown in FIG. 2. That is, the surface area of the erythrocyte is calculated as the sum of the projected surface area of the erythrocyte and the top-view surface area of the erythrocyte.

Meanwhile, the morphological functionality factor (f) of the erythrocyte is a ratio of the surface area of the erythrocyte with respect to the surface area of a sphere with a radius corresponding to that of the erythrocyte, and calculated by the mathematical formula 5 from the surface area (SA) of the erythrocyte.

$$f = \frac{SA}{S_s} = \frac{SA}{4\pi r^2} \qquad \text{[Mathematical Formula 5]}$$

Here, r is the radius of the erythrocyte, which is a value corresponding to the radius corresponding to the erythrocyte of the 3D image.

Also, a volume (V) of the erythrocyte is calculated by the mathematical formula 6 below.

$$V \cong \frac{p^2 \lambda \sum_{i=1}^{k} \sum_{j=1}^{l} \varphi(i,j)}{2\pi (n_{rbc} - n_m)} \qquad \text{[Mathematical Formula 6]}$$

Here, p is a length of one side of pixels forming the 3D image, k is a cross-sectional width of the part corresponding to the erythrocyte of the 3D image, l is a height of the part corresponding to the erythrocyte of the 3D image, $\varphi(i, j)$ is a phase value in radians of the part corresponding to the erythrocyte of the 3D image, $\lambda$ is a wavelength of a light source, $n_{rbc}$ is a refractive index of the erythrocyte, which is 1.396, and $n_m$ is a refractive index of a medium, which is 1.3334.

Meanwhile, sphericity index (SP) of the erythrocyte is a parameter which can determine the sphericity of the erythrocyte and is calculated by the mathematical formula 7.

$$SP = \frac{4\pi V^{2/3}}{(4\pi/3)^{2/3} SA} \qquad \text{[Mathematical Formula 7]}$$

Here, V is the volume of the erythrocyte described above, and SA is the surface area of the erythrocyte. According to the sphericity index, time elapsed since the blood collection may be estimated according to the sphericity index.

Morphological parameter values according to storage periods for various erythrocytes are shown in Table 1. The morphological parameters were calculated according to the measuring steps according to the present invention.

TABLE 1

| Property | | Storage time (days) | | | | | | | | | | |
|---|---|---|---|---|---|---|---|---|---|---|---|---|
| | | 8 | 13 | 16 | 23 | 27 | 30 | 34 | 37 | 40 | 47 | 67 |
| Profected surface area (PSA) (μm²) | Mean | 45 | 46 | 47 | 45 | 47 | 42 | 43 | 41 | 39 | 34 | 26 |
| | STD | 5 | 6 | 7 | 7 | 10 | 8 | 9 | 8 | 9 | 9 | 6 |
| Top-view surface area (TVSA) (μm²) | Mean | 81 | 81 | 89 | 83 | 84 | 85 | 84 | 81 | 81 | 79 | 81 |
| | STD | 8 | 8 | 9 | 8 | 8 | 8 | 9 | 7 | 6 | 8 | 10 |
| Surface area (μm²) | Mean | 126 | 127 | 136 | 128 | 131 | 127 | 127 | 122 | 120 | 113 | 107 |
| | STD | 11 | 14 | 16 | 16 | 17 | 16 | 11 | 12 | 13 | 14 | 15 |
| Volume (μm³) | Mean | 91 | 92 | 102 | 94 | 98 | 88 | 86 | 93 | 98 | 98 | 94 |
| | STD | 9 | 12 | 14 | 14 | 15 | 20 | 12 | 11 | 12 | 13 | 11 |
| Surface-to-volume ratio (SVR) (μm⁻¹) | Mean | 1.38 | 1.38 | 1.33 | 1.36 | 1.34 | 1.44 | 1.48 | 1.31 | 1.22 | 1.15 | 1.13 |
| | STD | 0.19 | 0.22 | 0.19 | 0.20 | 0.21 | 0.26 | 0.21 | 0.22 | 0.20 | 0.20 | 0.16 |
| Cell diameter (μm) | Mean | 7.76 | 7.77 | 7.76 | 7.63 | 7.70 | 7.45 | 7.65 | 7.52 | 7.25 | 6.73 | 6.04 |
| | STD | 0.49 | 0.55 | 0.53 | 0.58 | 0.58 | 0.69 | 0.75 | 0.75 | 0.86 | 0.89 | 0.68 |
| k factor | Mean | 0.88 | 0.78 | 0.66 | 0.84 | 0.70 | 0.70 | 0.93 | 0.93 | 1.03 | 1.20 | 1.35 |
| | STD | 0.18 | 0.19 | 0.21 | 0.22 | 0.23 | 0.37 | 0.30 | 0.56 | 0.34 | 0.36 | 0.41 |
| f factor | Mean | 0.66 | 0.69 | 0.72 | 0.70 | 0.70 | 0.73 | 0.69 | 0.69 | 0.73 | 0.79 | 0.93 |
| | STD | 0.07 | 0.09 | 0.10 | 0.10 | 0.10 | 0.13 | 0.17 | 0.14 | 0.15 | 0.16 | 0.16 |
| Sphericity index | Mean | 0.78 | 0.78 | 0.78 | 0.78 | 0.79 | 0.75 | 0.74 | 0.81 | 0.86 | 0.91 | 0.94 |
| | STD | 0.07 | 0.08 | 0.07 | 0.08 | 0.07 | 0.08 | 0.08 | 0.09 | 0.09 | 0.10 | 0.09 |

Here, Mean is an average of each parameter of the erythrocytes used as samples, and STD is a variation of each parameter of the erythrocytes used as samples. Here, k factor is a sphericity coefficient of the erythrocyte, and f factor is a morphological functionality factor of the erythrocyte.

Figure 4:
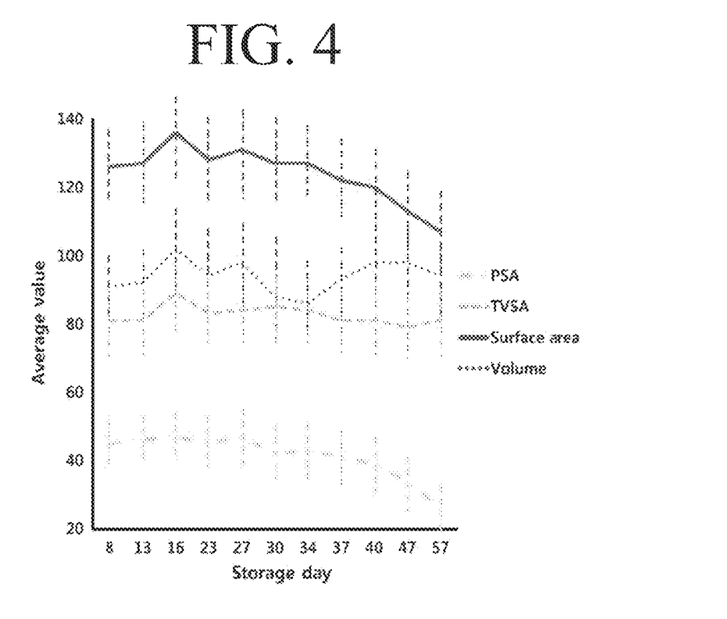
FIGS. 4 to 6 are graphs showing changes of morphological parameter values over a storage period, which are calculated by the erythrocyte test method according to the present invention.
Figure 5:
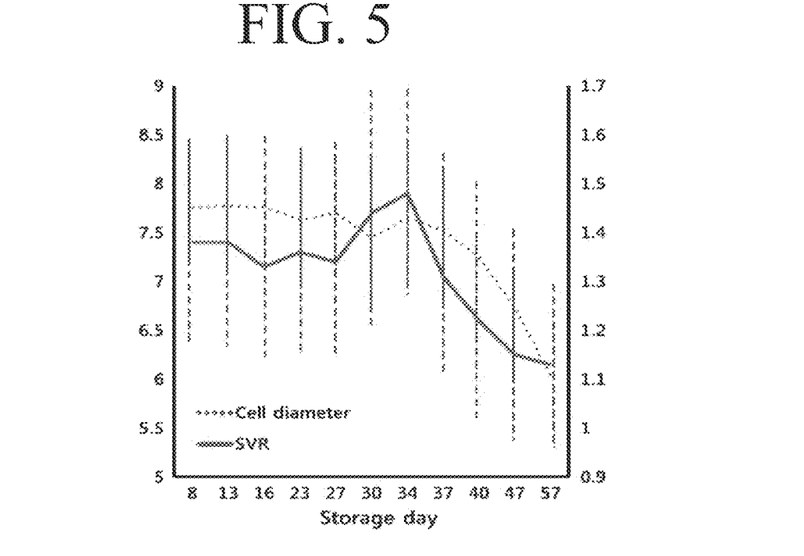
Figure 6:
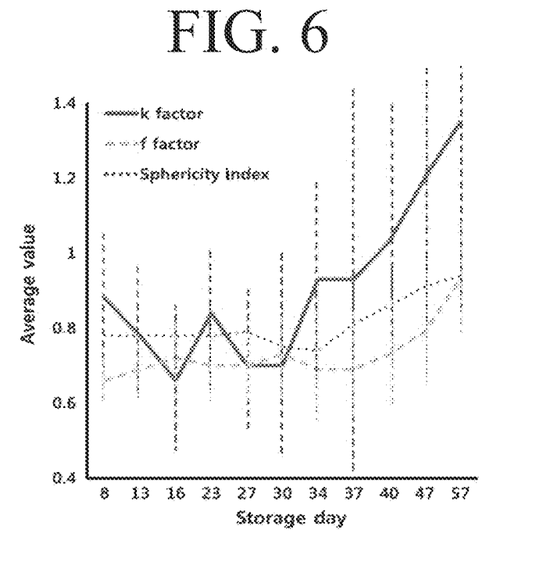

Meanwhile, in FIGS. 4 to 6, parameters shown in Table 1 are illustrated in graphs. FIG. 4 is a graph showing the projected surface area (PSA) of an erythrocyte according to a storage period, the top-view surface area (TVSA) of a 3D image, the surface area (SA) of an erythrocyte, and the volume of an erythrocyte, FIG. 5 is a graph showing the diameter and the surface-to-volume ratio (SVR) of an erythrocyte according to a storage period, and FIG. 6 is a graph showing the sphericity coefficient (k) of an erythrocyte, the morphological functionality factor (f) of an erythrocyte, and the sphericity index of an erythrocyte according to a storage period.

Referring to the table and the drawings, while the top-view surface area (TVSA) of the 3D image and the erythrocyte volume show relatively small changes within the storage period, the surface area and the projected surface area (PSA) of the erythrocyte begin to decrease after 30 days of storage. Also, the diameter and SVR of the erythrocyte are not significantly changed in the early stage of storage but drastically decrease after 35 days. In addition, the sphericity coefficient (k), the morphological functionality factor (f), and the sphericity index of an erythrocyte are dramatically increased after 34 days of storage. Therefore, to calculate the storage period or freshness of erythrocytes, any one of the morphological parameters such as the sphericity coefficient (k), the morphological functionality factor (f), the sphericity index, the surface area, the projected surface area (PSA), diameter and SVR of an erythrocyte may be used.

Figure 7:
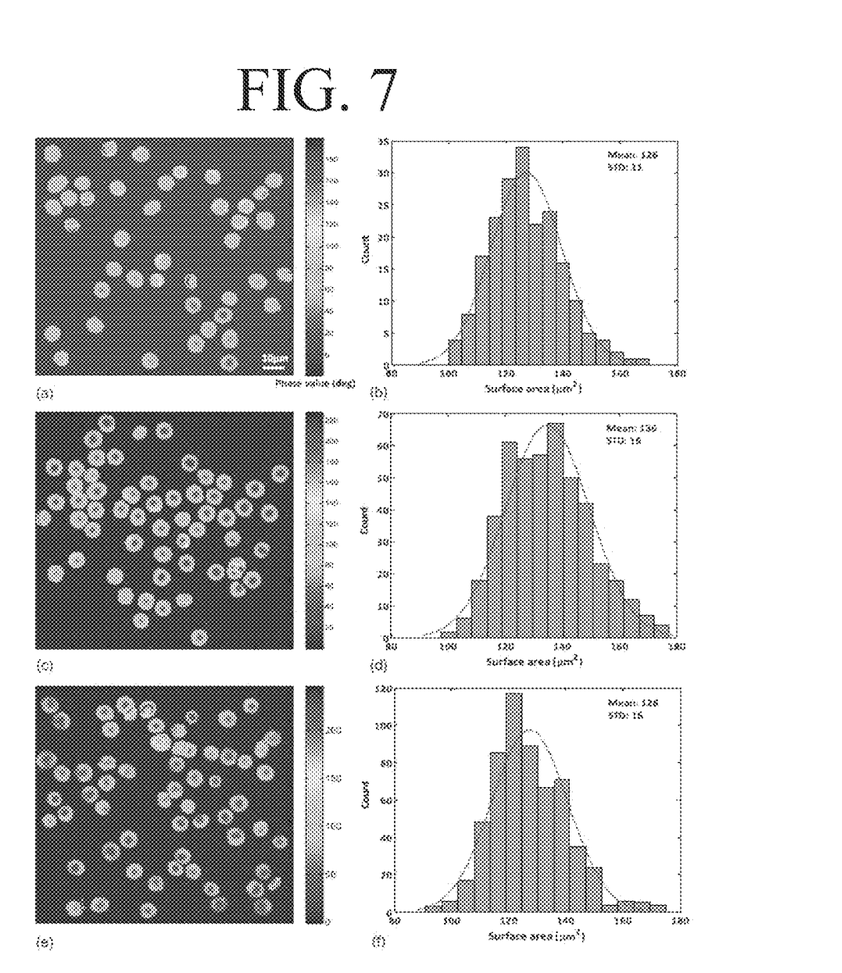
FIGS. 7 and 8 are 3D maps and surface area histograms of erythrocytes according to a storage period.
Figure 8:
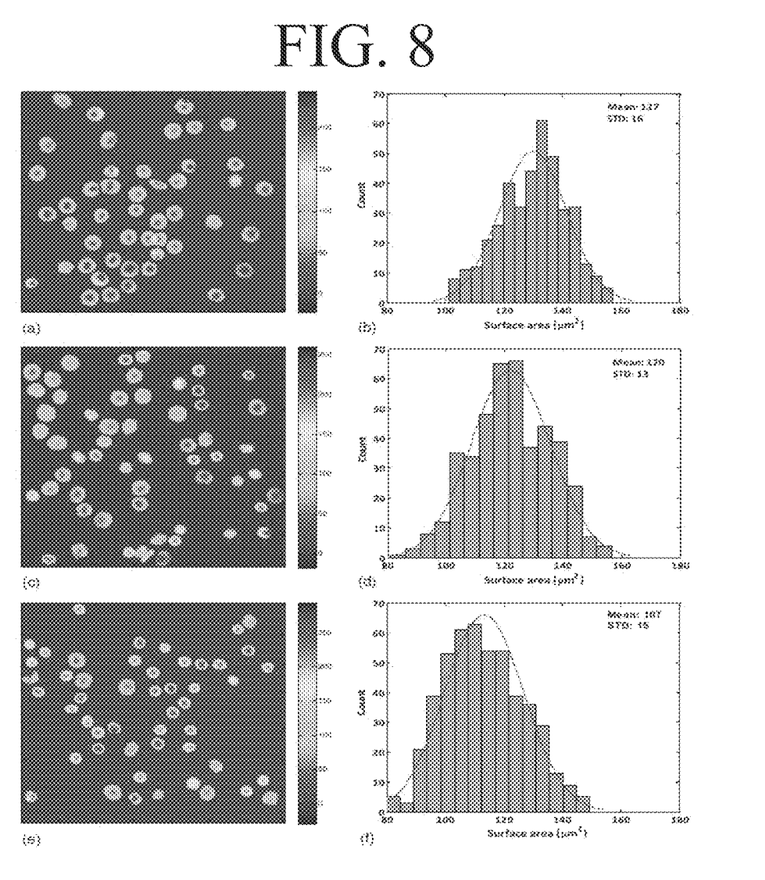

Meanwhile, FIGS. 7 and 8 show 3D maps of erythrocytes according to storage period and surface area histograms. In FIG. 7, (a), (c) and (e) are 3D maps for erythrocyte samples at storage periods of day 8, 16 and 23, and (b), (d) and (f) are surface area histograms for the erythrocyte samples at day 8, 16 and 23, respectively. In FIG. 8, (a), (c) and (e) are 3D maps for erythrocyte samples at storage periods of day 30, 40 and 57, and (b), (d) and (f) are surface area histograms for erythrocyte samples at storage periods of day 30, 40 and 57. Referring to FIGS. 7 and 8, although until the storage period of day 23, the surface area of the erythrocyte shows a relatively insignificant change, after day 30, the surface area of the erythrocyte is decreased, and the number of erythrocytes having a relatively small surface area may also be increased.

Meanwhile, the prediction step (S103) is for predicting the state such as the storage period or freshness of the erythrocyte based on the morphological parameters measured in the parameter measuring step (S102). An examiner predicts the storage period and freshness of the erythrocyte based on the measured morphological parameter value, and at least one of the sphericity coefficient (k), the morphological functionality factor (f), the sphericity index, the surface area, the projected surface area (PSA), the diameter and SVR of the erythrocyte may be used. Here, the examiner may predict the erythrocyte state by collecting data on each morphological parameter value according to a storage period through multiple tests and comparing the measured morphological parameter value with the collected data.

The morphological cell parameter-based erythrocyte test method according to the present invention described above is for performing modeling of a 3D image for an erythrocyte to be tested and measuring morphological parameters of the erythrocyte based on the 3D image. Therefore, time and effort consumed in measuring may be reduced, and accuracy of the measurement is excellent.

Meanwhile, the morphological cell parameter-based erythrocyte test method according to the present invention may predict different storage periods for numerous erythrocyte samples since blood collection. In the modeling step (S101), numerous erythrocyte samples were used for modeling of 3D images, respectively, in the parameter measuring step (S102), morphological parameters for each erythrocyte sample were measured based on the 3D image of each erythrocyte sample, and in the prediction step (S103), a storage period of the erythrocyte sample since the blood collection is predicted based on the morphological parameters of the erythrocyte sample. Here, in the prediction step (S103), when sufficient data on the morphological parameter value according to a storage period is gained, storage period of each erythrocyte sample may be more accurately predicted. Even when the date on the morphological parameter value according to a storage period is insufficient, the storage periods of the erythrocyte samples may relatively be easily compared.

A morphological cell parameter-based erythrocyte test method according to the present invention can be used in 3D image modeling for an erythrocyte to be tested and measurement of morphological parameters of the erythrocyte based on the 3D image. Therefore, time and effort consumed for measurement can be reduced, and measurement accuracy is excellent.

Description of the disclosed exemplary embodiments is provided to those of ordinary skill in the art to use or realize the present invention. Various modifications for such exemplary embodiments are apparent to those of ordinary skill in the art, and general principles defined herein may be applied to other exemplary embodiments without departing from the scope of the invention. Therefore, while the present invention has been shown and described with reference to certain exemplary embodiments thereof, it will be understood that the present invention be interpreted in the broadest scope corresponding to the principles and new characteristics disclosed herein.

DESCRIPTION OF REFERENCE NUMERALS

S101: Modeling step
S102: Parameter measuring step
S103: Prediction step
100: Digital holographic microscopy
110: Setting plate
111: Penetration plate
112: Spacing member
120: Beam splitter
130: Imaging unit

What is claimed is:

1. A morphological cell parameter-based erythrocyte test method, comprising:
   generating an optical interference signal from an object beam passing through an erythrocyte to be tested and a reference beam emitted from a light source unit;
   creating a holographic image of the optical interference signal using an imaging unit;
   creating a three-dimensional (3D) image of the erythrocyte based on the holographic image;
   measuring morphological parameters of the erythrocyte through the 3D image; and
   determining a state of the erythrocyte based on the morphological parameters,
   wherein the morphological parameters includes a surface area of the erythrocyte, which is the sum of a projected surface area of the erythrocyte and a top-view surface area of the part corresponding to the erythrocyte of the 3D image.

2. The method of claim 1, wherein the 3D image is obtained from the erythrocyte to be tested by using a digital holographic microscopy.

3. The method of claim 1, wherein the object beam passes through the erythrocyte from bottom to top.

4. The method of claim 1,
   wherein the erythrocyte is a disc-shaped erythrocyte having a predetermined radius, and
   wherein the object beam is penetrated through the erythrocyte in a direction crosslinked with the predetermined radius of the disc-shaped erythrocyte to create a holographic image of a concave part in the middle of the disc-shaped erythrocyte.

5. The method of claim 3, wherein the morphological parameters includes a morphological functionality factor of the erythrocyte, which is a ratio of the surface area of the erythrocyte to a surface area of a sphere with a radius corresponding to the radius of the erythrocyte.

6. The method of claim 1, wherein the projected surface area (PSA) of the part corresponding to the erythrocyte of the 3D image is calculated by the mathematical formula below:

$$PSA = Np^2$$

where p is the length of one side of pixels forming the 3D image and N is the number of pixels in the range corresponding to the erythrocyte of the 3D image.

7. The method of claim 5, wherein the surface area ($S_S$) of the sphere with a radius corresponding to the radius of the erythrocyte is calculated by the mathematical formula below:

$$S_S = 4\pi r^2$$

where r is the radius of the erythrocyte.

8. The method of claim 7, wherein the radius (r) of the erythrocyte is calculated by the mathematical formula below:

$$r \cong \sqrt{\frac{PSA}{\pi}}$$

where PSA is a projected surface area of the part corresponding to the erythrocyte of the 3D image, which is a value obtained by multiplying the square of one side length of a pixel forming the 3D image by the number of pixels forming the 3D image.

9. The method of claim 3, wherein the morphological parameters includes a sphericity index (SP) calculated from a volume (V) of the 3D image and the surface area (SA) of the erythrocyte, by the mathematical formula below:

$$SP = \frac{4\pi V^{2/3}}{4\pi/3^{2/3} SA}.$$

10. The method of claim 3, wherein the morphological parameters includes the projected surface area (PSA) of the erythrocyte calculated from a length (p) of one side of pixels in the 3D image and the number (N) of pixels forming the part corresponding to the erythrocyte of the 3D image, by the mathematical formula below:

$$PSA = Np^2.$$

11. The method of claim 1, wherein,
in the creating of a 3D image of the erythrocyte, a 3D image of each erythrocyte sample of a plurality of erythrocyte samples is created,
in the measuring morphological parameters of the erythrocyte, morphological parameters of the each erythrocyte sample is measured based on the 3D image of the each erythrocyte sample, and
in the determining of the state of the erythrocyte, a storage period of the each erythrocyte sample since blood collection is determined based on the morphological parameters of the each erythrocyte sample.

* * * * *